US012588913B2

(12) United States Patent
Pheil et al.

(10) Patent No.: US 12,588,913 B2
(45) Date of Patent: Mar. 31, 2026

(54) BONE GRAFT HARVESTING APPARATUS

(71) Applicant: Medline Industries, LP, Northfield, IL (US)

(72) Inventors: Natan Pheil, Highland Park, IL (US); Dinesh Koka, Winter Park, FL (US); Samuel Nader, Arlington Heights, IL (US)

(73) Assignee: Medline Industries, LP, Northfield, IL (US)

( * ) Notice: Subject to any disclaimer, the term of this patent is extended or adjusted under 35 U.S.C. 154(b) by 173 days.

(21) Appl. No.: 18/237,723

(22) Filed: Aug. 24, 2023

(65) Prior Publication Data

US 2025/0064460 A1 Feb. 27, 2025

(51) Int. Cl.
| | |
|---|---|
| *A61B 17/16* | (2006.01) |
| *A61F 2/46* | (2006.01) |
| *A61B 17/00* | (2006.01) |

(52) U.S. Cl.
CPC ........ *A61B 17/1635* (2013.01); *A61F 2/4644* (2013.01); *A61B 2017/00367* (2013.01)

(58) Field of Classification Search
CPC .............. A61B 17/1635; A61B 10/025; A61B 17/1637
See application file for complete search history.

(56) References Cited

U.S. PATENT DOCUMENTS

| | | | |
|---|---|---|---|
| 4,951,690 | A | 8/1990 | Baker |
| D358,082 | S | 5/1995 | Trezza |
| 5,439,467 | A | 8/1995 | Benderev |
| 5,556,399 | A | 9/1996 | Huebner |
| 5,730,752 | A | 3/1998 | Alden |
| 5,833,628 | A | 11/1998 | Yuan |
| 5,954,671 | A | 9/1999 | O'Neill |
| 6,139,509 | A | 10/2000 | Yuan |
| D458,817 | S | 6/2002 | Jenkins |
| 6,485,495 | B1 * | 11/2002 | Jenkinson .............. A61B 17/32 |
| | | | 606/167 |
| D585,989 | S | 2/2009 | Leroy |
| D615,196 | S | 5/2010 | Doll |
| D629,896 | S | 12/2010 | Horton |
| 9,277,927 | B2 | 3/2016 | Khanna |
| D803,396 | S | 11/2017 | Oberkircher |
| 10,292,688 | B2 | 5/2019 | Marino |
| D871,870 | S | 1/2020 | Owen |

(Continued)

OTHER PUBLICATIONS

Arthrex, Brochure for OsteoAugerTM Bone Graft Harvesting System, Dec. 6, 2021.

(Continued)

*Primary Examiner* — Andrew Yang
(74) *Attorney, Agent, or Firm* — Fitch, Even, Tabin & Flannery LLP

(57) ABSTRACT

Disclosed is a bone graft harvesting device that includes a cutter section and a housing section secured to one another via a removable fastener, such as a manually operable screw. One of these sections includes a proximal end having a shaft configured for connection to a drill or other rotary tool, and the other may include a scoop for facilitation of removal of harvested bone from a patient. The cutter section and housing section may be separated from one another upon harvesting of bone from a patient to access harvested bone in a cavity of the housing.

9 Claims, 9 Drawing Sheets

(56) References Cited

U.S. PATENT DOCUMENTS

| | | |
|---|---|---|
| 11,185,339 B2 | 11/2021 | Perez |
| D1,006,226 S | 11/2023 | Goode |
| D1,069,118 S | 4/2025 | Dutton |
| 2003/0181926 A1 | 9/2003 | Dana |
| 2004/0044365 A1 | 3/2004 | Bachman |
| 2008/0177200 A1 | 7/2008 | Ikehara |
| 2015/0045799 A1 | 2/2015 | Budyansky |
| 2019/0090868 A1 | 3/2019 | Bracy |
| 2019/0388100 A1 | 12/2019 | Perez |
| 2020/0390434 A1 | 12/2020 | Fu |
| 2022/0071641 A1 | 3/2022 | Perez |
| 2025/0064460 A1 | 2/2025 | Pheil |

OTHER PUBLICATIONS

Arthrex, Brochure for OsteoAugerTM Bone Graft Harvesting System, Jun. 2, 2022.

Autograft Harvester, medlineunite.com, [online], [site visited Oct. 9, 2025], Available from internet, URL: https://medlineunite.com/producUautograft-harvester/ (Year: 2025).

Bone Graft Harvest System Brochure, paragon28.com, first available date 2023 [online], [site visited Oct. 9, 2025], Available from internet, URL: https://paragon28.com/app/uploads/2024/03/HARV-01-RevD_Bone-Graft-Harvest-System-Brochure.pdf (Year: 2023).

Screen captures from YouTube video clip entitled "Bone Graft Harvest System Animation," uploaded on May 10, 2019 by user" Paragon 28". Retrieved from Internet <https://www.youtube.com/watch?v=h5GKVnDimZY> (Year: 2019).

Titanium EDC Tactical WAND Portable SURVIVAL Tool, dhgate.com, [online], [site visited Oct. 9, 2025], Available from internet, URL: https://www.dhgate.com/goods/901434015.html (Year: 2025).

* cited by examiner

BONE GRAFT HARVESTING APPARATUS

TECHNICAL FIELD

The disclosure in the field of devices and methods for surgical procedures, especially bone and joint repair.

BACKGROUND

In repairing a bone fracture or in a joint fusion procedure, it is common for an orthopedic device such as a bone plate to be placed over the fracture in the bone or across the fusion site, and for fasteners such as screws to then be implanted in bone on either side of the fracture or joint. Many types of orthopedic devices are known for such purposes. In some cases, it can be desirable to introduce morselized bone harvested from another region of the patient's body, such as the calcaneus, distal and proximal tibia, iliac crest, or distal radius, to facilitate healing of the fracture or remodeling of the joint. Various bone graft harvesting devices have been described in the art.

A bone graft harvesting device is now provided. The device is an assembly that includes a separable cutter section and housing section, where the cutter section and housing section together define a hollow bone-receiving chamber when assembled, and a fastener that may be disengaged. The cutter section is equipped with an auger portion at the distal end of the device. One of the cutter and housing sections is provided with a proximal shaft for connection to a rotary tool such as a drill.

The device may be mounted to a rotary tool and used to harvest bone from a patient. Upon harvesting of the bone, the surgeon may disengage the fastener to separate the cutter section and housing section. This will expose the harvested bone to facilitate recovery thereof while allowing the section with the proximal shaft to remain connected to the rotary tool. This enables the surgeon to recover bone and reassemble the device for additional bone harvesting without removing the shaft from the rotary tool. The other section of the device may be provided with a scoop sized to fit within an interior cavity of the other section to enable recovery of the harvested bone via a scooping action. The cutter section and housing section may be provided with respective keyed geometries to assist in reassembly and to resist torsional separation of these sections when the device is subjected to frictional torque.

DETAILED DESCRIPTION

Figure 1:
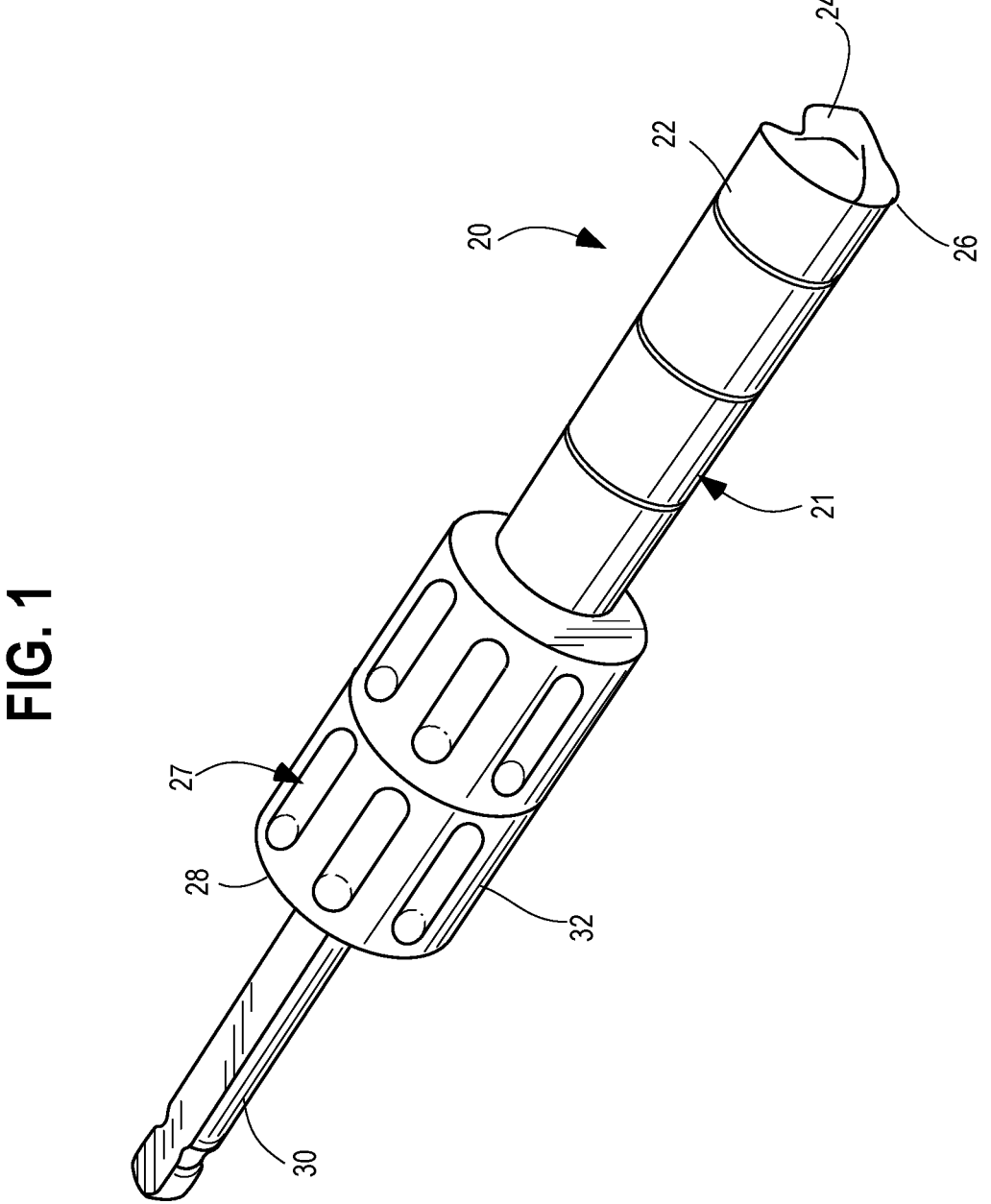
FIG. 1 is a perspective view of a prior art bone graft harvesting device comprising an auger portion and a separable shaft portion.
Figure 2:
FIG. 2 is a perspective view of the prior art bone graft harvesting device shown in FIG. 1 with the shaft portion decoupled from the auger portion.

The prior art bone graft harvesting device 20 depicted in FIG. 1 includes an auger portion 21 having a tubular region 22 defining a bone-receiving chamber. The device terminates in an auger tip 24 at the distal end 26. The auger portion 21 is proximally connected to a shaft portion 27 having itself a proximal end 28 provided with an AO coupling quick release shaft 30. The shaft 30 is connectable to a rotary tool such as a drill (not shown in FIG. 1). The device is used to drill into the bone of a patient to harvest bone for grafting purposes. Upon harvesting bone from a patient, the shaft portion 27 is manually decoupled from the auger portion 21 via manually unscrewing the knurled coupling nut 32. A pusher 33 (FIG. 2) is then inserted into the distal end 26 of the auger portion 21 and used to push the recovered bone, typically in morselized form, from the auger portion 21, into receiving tray 23.

Figure 3:
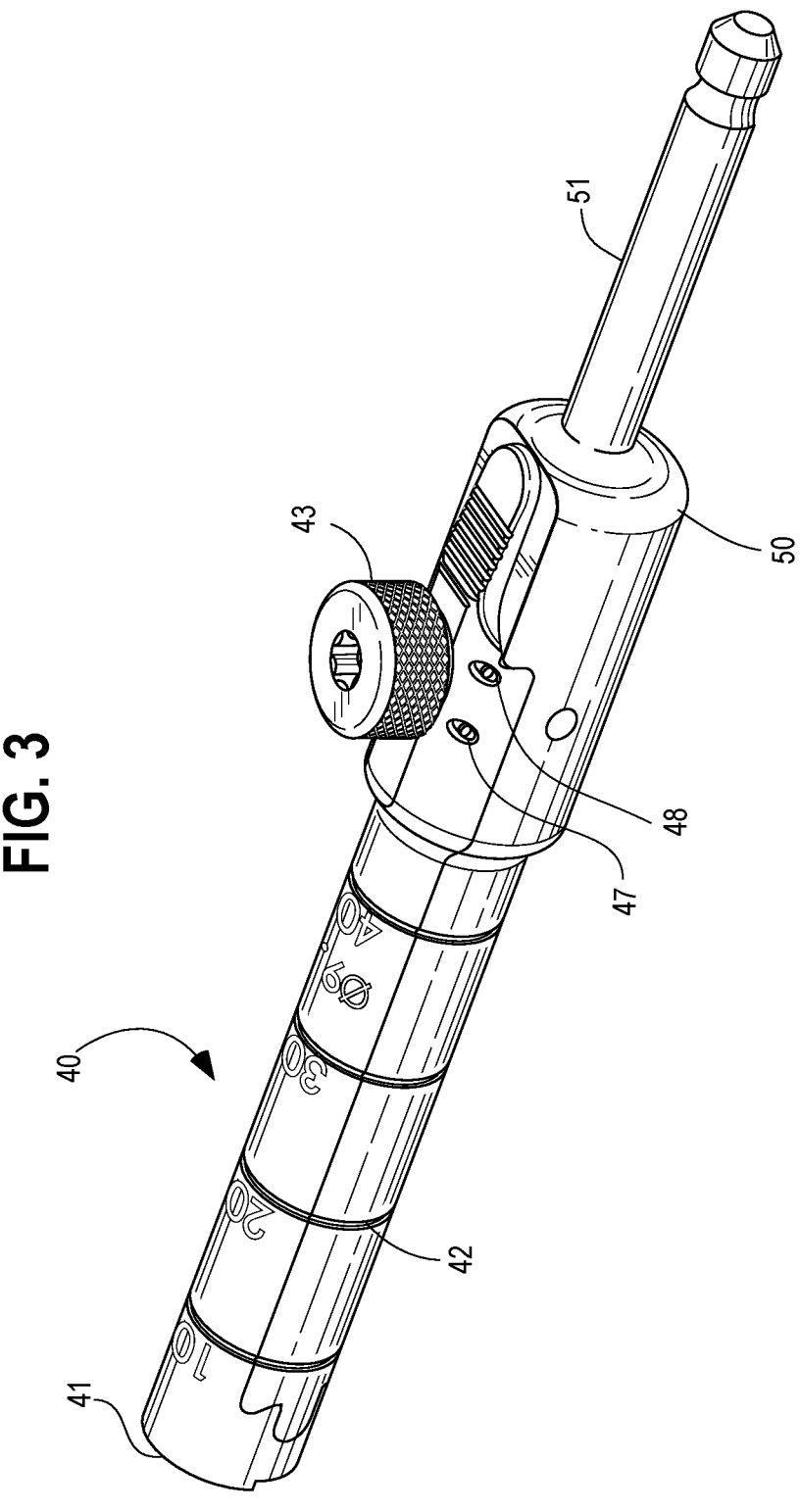
FIG. 3 is a perspective view of a representative inventive bone graft harvesting device.
Figures 4, 5:
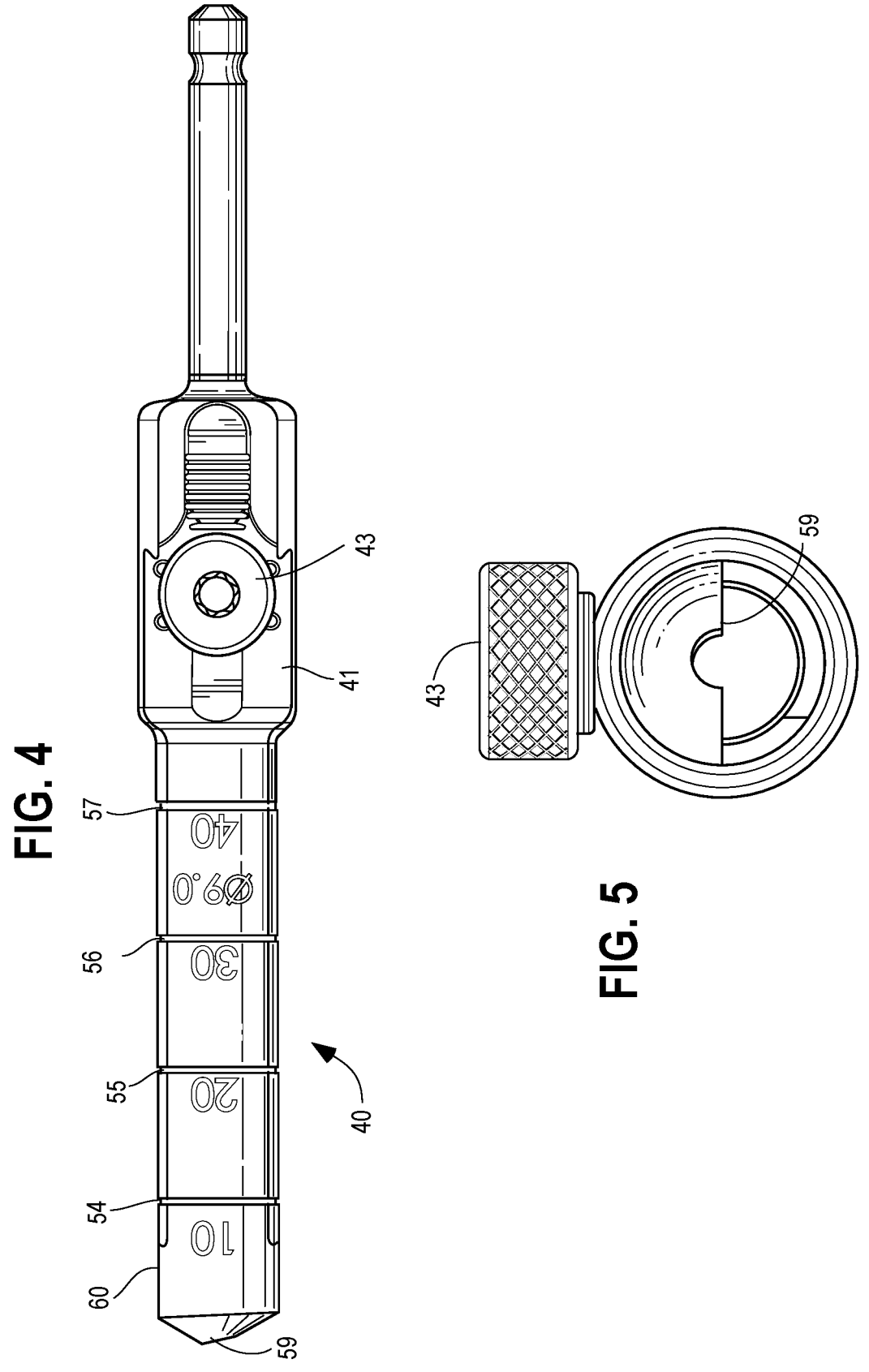
FIG. 4 is a top plan view of the bone graft harvesting device shown in FIG. 3.
FIG. 5 is a front elevation view of the bone graft harvesting device shown in FIG. 3.

With reference now to FIGS. 3-9, the illustrated exemplary bone graft harvesting device 40 includes a cutter section 41 and a housing section 42 connected and secured to one another via a thumb screw 43. The thumb screw 43 is captured by dowel pins 47, 48 in the cutter section 41 (FIG. 3). The proximal end 50 of the housing section 42 is provided with a shaft 51, which, in the illustrated embodiment, is an AO coupling shaft for quick-release connection to a rotary tool such as a drill (not shown). Graduations 54, 55, 56, 57 (FIG. 4) are provided with corresponding label indicia to indicate to a surgeon the depth of insertion of the device 40. The cutter section 41 is provided with an auger portion 59 at its distal end 60. The auger portion may be otherwise conventional and should in any case include a sharp edge suitable for cutting into and harvesting bone.

Figures 9, 10:
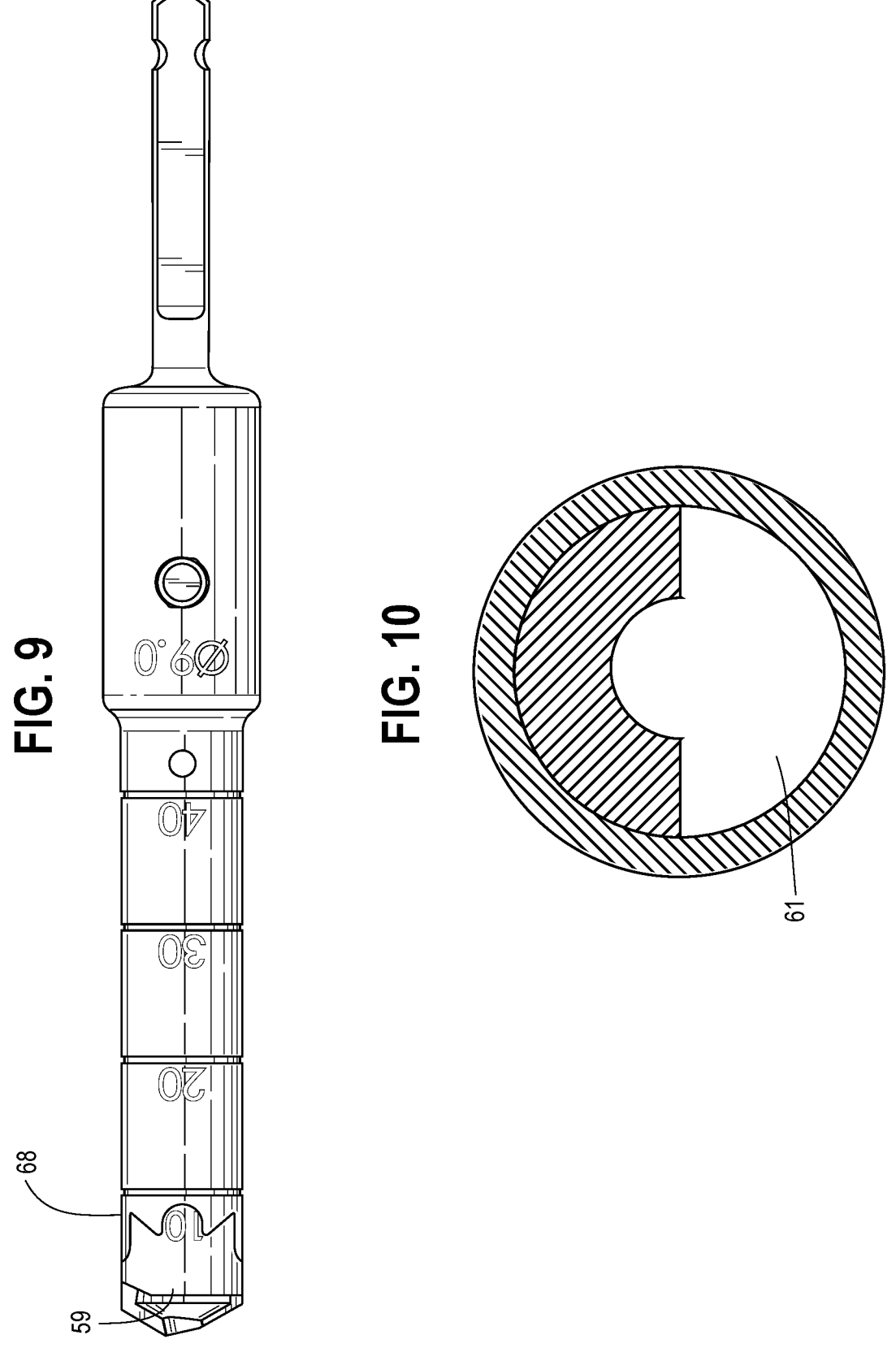
FIG. 9 is a bottom plan view of the bone graft harvesting device depicted in FIG. 3.
FIG. 10 is a cross-sectional view taken along line 10-10 in FIG. 7
Figure 11:
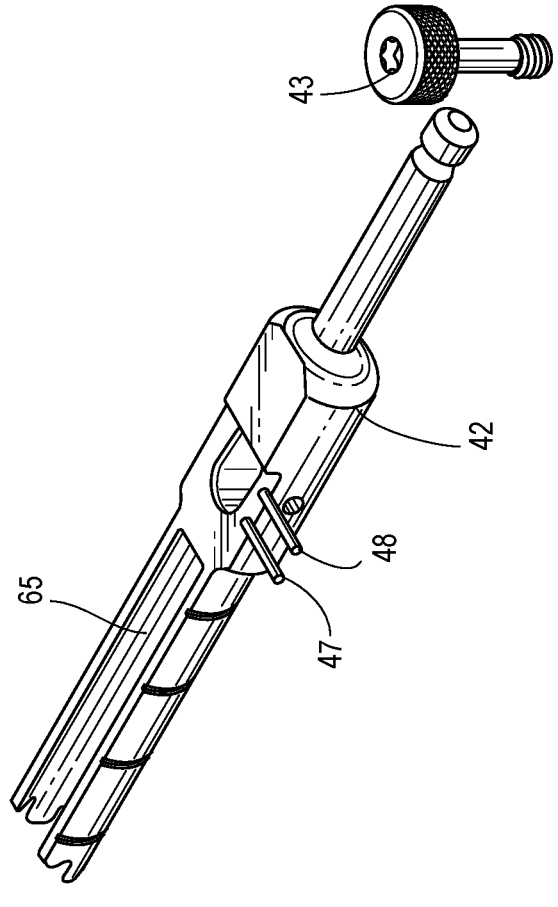
FIG. 11 is an exploded view of the bone graft harvesting device shown in FIG. 3.
Figure 11:
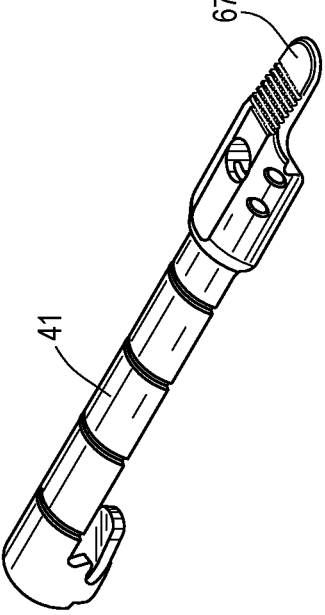
Figure 12:
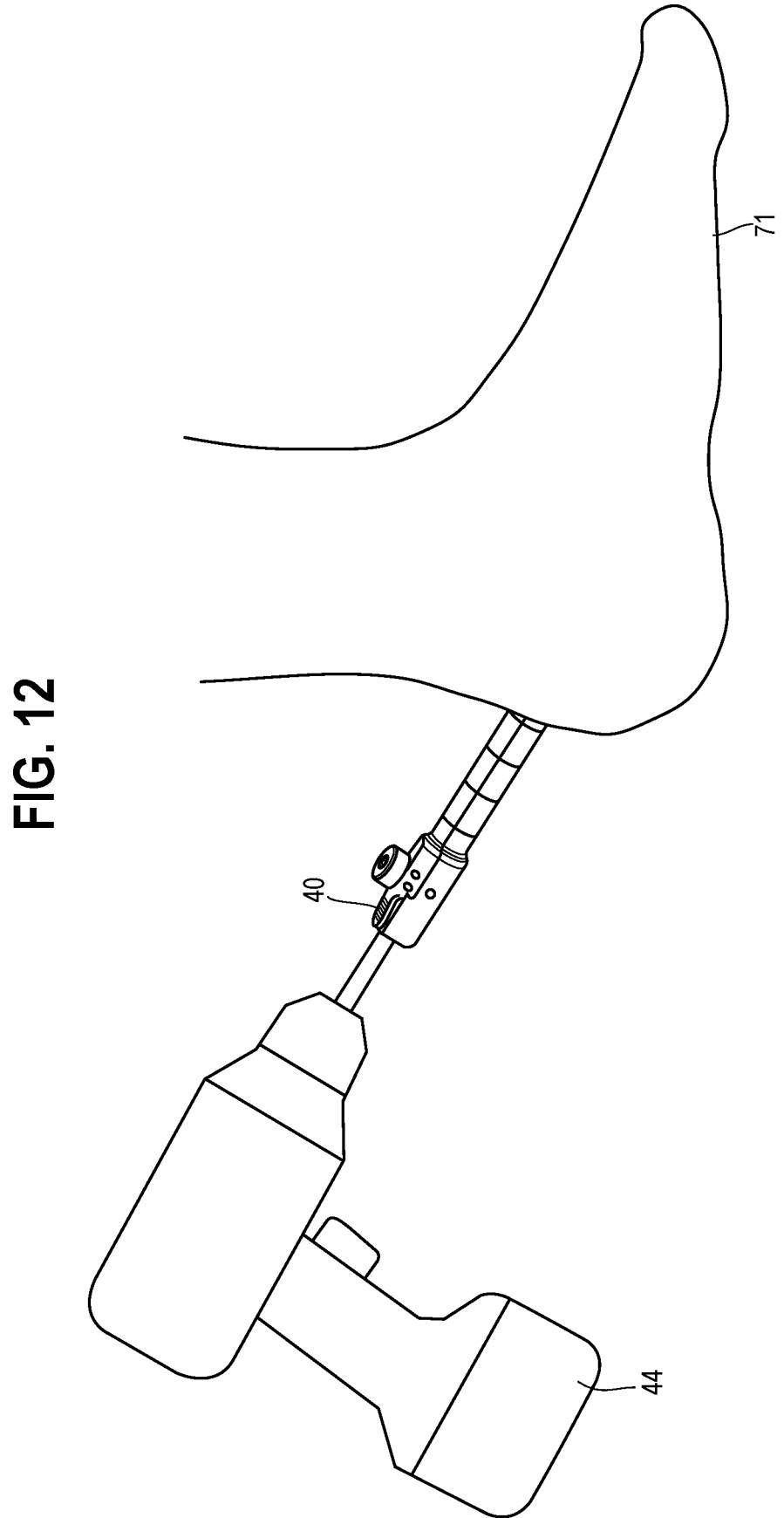
FIG. 12 is a representative view illustrating the bone graft harvesting device of FIG. 3 in position for harvesting bone from a patient.

When assembled, the cutter section 41 and the housing section 42 define a bone-receiving chamber 61, seen in FIG. 10. When coupled to a rotary tool 44 (FIG. 12, not to scale), the cutter section 41 and housing section 42 are integral and the device 40 can be operated to harvest bone from a suitable area of the patient 71. The bone is removed and typically becomes morselized via the action of the auger portion 59, and the so-harvested bone is retained within the bone-receiving chamber 61. This operation is seen representationally in FIG. 12.

Figure 13:
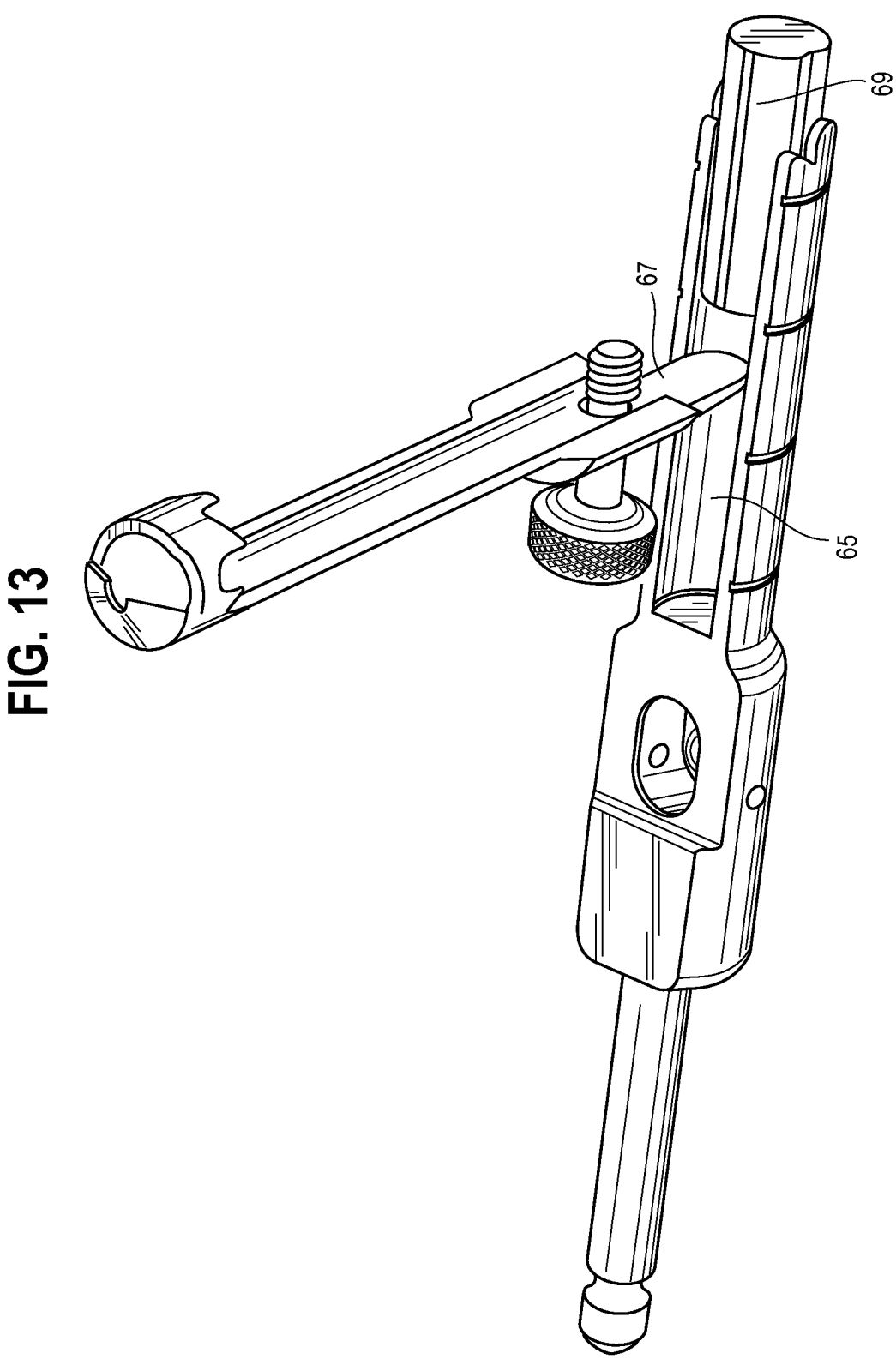
FIG. 13 is a perspective view showing the above-depicted bone graft harvesting device after bone has been harvested and the device opened to allow removal of the harvested bone therefrom.

As seen in FIG. 13, when sufficient bone has been harvested or when the surgeon otherwise desires, the rotary tool is depowered and the surgeon manually separates the cutter section 41 and housing section 42 by unscrewing the thumb screw 43, which is provided with a knurled surface 64 to facilitate grasping. The cutter section 41 is removed leaving the morselized bone 69 within a cavity 65 of the housing section 42, the cavity 65 partially defining the bone-receiving chamber. The bone 69 is represented as a plug but in practice often would consist of dissociated bone fragments. As seen, upon separation of the cutter section 41 from the housing section 42, the bone-receiving chamber is completely opened to facilitate access to the harvested bone contained therewithin. The housing section that contains the harvested bone can remain connected to the rotary tool while the cutter section is removed and the bone subsequently recovered from the device.

The cutter section 41 is provided with an integral scoop 67 that is sized to fit within the cavity 65 and that preferably has a terminal geometry that corresponds to the interior geometry of the cavity 65. In the illustrated embodiment, the scoop 67 has an externally radiused end that corresponds to the interior radiused surface of the cavity 65. This allows the surgeon to use a scooping action to recover harvested bone cleanly from the device.

Figures 6, 7, 8:
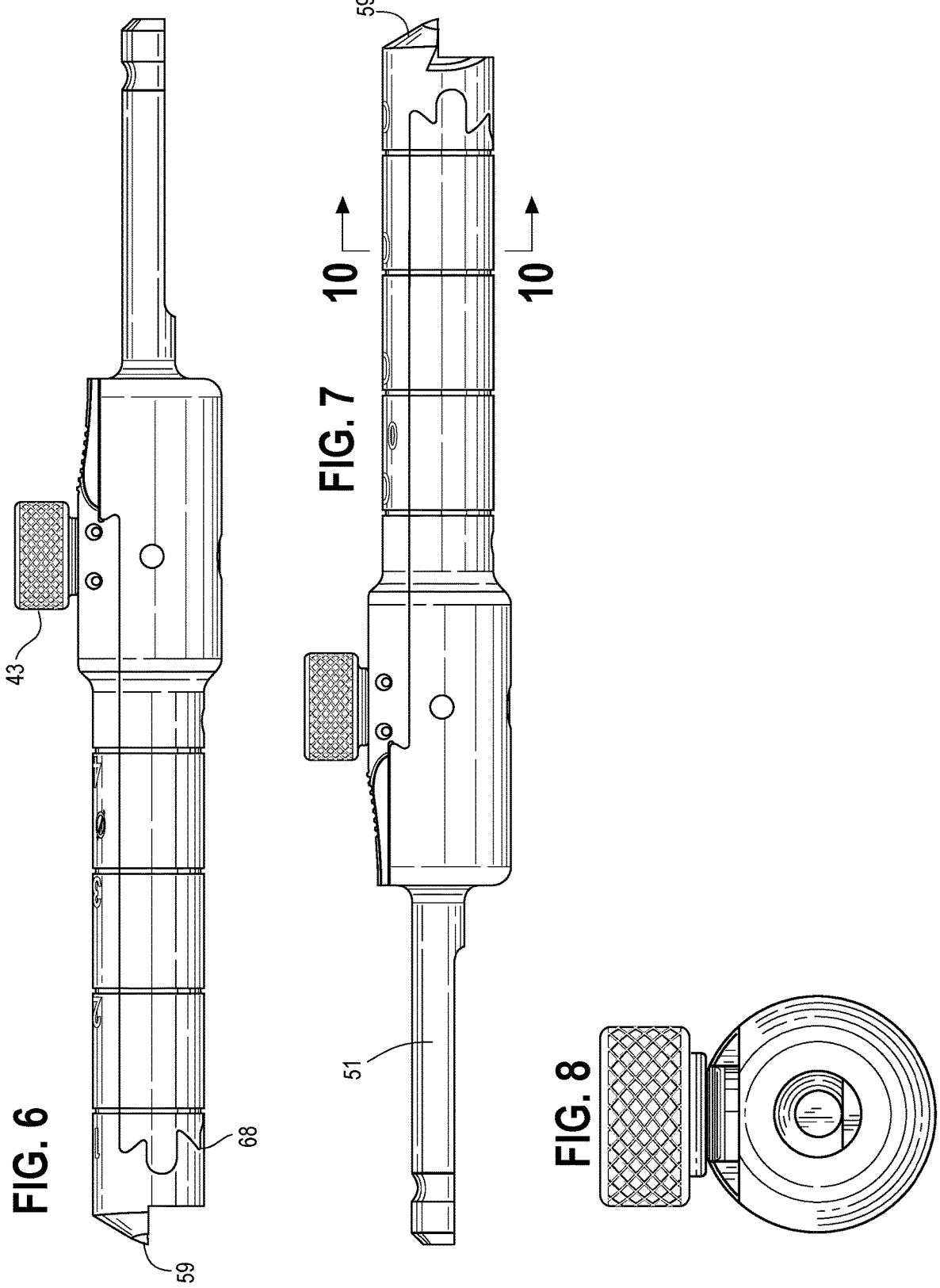
FIG. 6 is a first side elevation view of the bone graft harvesting device shown in FIG. 3.
FIG. 7 is a second side elevation view of the bone graft harvesting device shown in FIG. 3.
FIG. 8 is a rear elevation view of the bone graft harvesting device shown in FIG. 3.

With reference to FIGS. 6, 7, and 9, the housing section 41 and cutter section 42 are provided respectively with complementary keyed geometries seen at interface 68. One purpose of the keyed geometries is to enable quick repositioning of the cutter section and housing section for reassembly of the device should the surgeon require an additional bone harvesting operation. A second purpose is to form a radially interlaced structure that resists torsional separation of the cutter and housing sections when the device is subjected to frictional torque as the auger portion 59 engages the bone of a patient.

The illustrated device has the shaft 51 disposed on the housing section 42 and the scoop 67 disposed on the cutter section 41, but in practice the position of these may be reversed. Similarly, the fastener is shown as a manual thumb screw 43, but other types of fasteners may be employed.

The cutter section is preferably made of metal. The housing section may be made of metal or a suitable plastic material. Generally, the device is intended as a single use device sold in a sterile package (not shown) but it is contemplated that a durable, re-usable device could be provided in some embodiments. The device may be provided such that the housing section and cutter section define a circular cylindrical form having in any diameter suitable for harvesting bone from the calcaneus, distal and proximal tibia, iliac crest, distal radius, or other suitable site, such as a diameter of 6 mm, 8 mm, or 10 mm. Other dimensions and geometries may also be suitable.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A bone graft harvesting device comprising an assembly of a cutter section and a separable housing section and a fastener securing the cutter section to the housing section, one of the housing section and cutter section comprising a proximal shaft, the cutter section and housing section defining therebetween a hollow bone-receiving chamber, said cutter section including an auger portion disposed at a distal end of the device, wherein the cutter section and housing section are joined at an interface that is an exterior interface along at least a portion of a path that extends from a proximal end of the assembly to the distal end of the assembly.

2. The device of claim 1, the fastener comprising a manually operable screw.

3. The device of claim 1, the proximal shaft being disposed on the housing section.

4. The device of claim 3, the cutter section including a scoop portion sized to fit inside the housing section when the cutter section and housing section have been separated.

5. The device of claim 1, the cutter section and housing section each provided with a keyed geometry proximal said distal end, the geometry of the cutter section being complementary to that of the housing section.

6. The device according to claim 1, said proximal shaft comprising an AO coupling.

7. A method comprising providing the device of claim 1, connecting said device to a rotary tool via said proximal shaft, harvesting bone from a patient, separating said cutter section from said housing section, and recovering harvested bone.

8. A method according to claim 7, the housing section comprising the proximal shaft, the method comprising separating the cutter section from the housing section while the proximal shaft remains connected to said rotary tool.

9. A method comprising:
   providing a bone harvesting device, the device comprising an assembly of a cutter section and a separable housing section and a fastener securing the cutter section to the housing section, the housing section comprising a proximal shaft, the device including a hollow bone-receiving chamber, said cutter section including an auger portion disposed at a distal end of the device, wherein the cutter section and housing section are joined at an interface that is an exterior interface along at least a portion of a path that extends from a proximal end of the assembly to the distal end of the assembly;
   connecting said device to a rotary tool via said proximal shaft;
   harvesting bone from a patient;
   separating said cutter section from said housing section, and recovering harvested bone from the housing section of the device while the proximal shaft remains connected to said rotary tool.

\* \* \* \* \*